United States Patent [19]

Andrean et al.

[11] Patent Number: 5,449,403
[45] Date of Patent: Sep. 12, 1995

[54] PRODUCT BASED ON COLORED INORGANIC PARTICLES INCLUDING A MELANIN PIGMENT, PROCESS FOR ITS PREPARATION AND ITS USE IN COSMETICS

[75] Inventors: Hervé Andrean, Paris; Alex Junino, Livry-Gargan; Jean P. Arraudeau, Paris, all of France

[73] Assignee: L'Oreal, Paris, France

[21] Appl. No.: 119,081

[22] Filed: Jan. 3, 1994

[30] Foreign Application Priority Data

Jan. 16, 1992 [FR] France ................... 92 00415

[51] Int. Cl.⁶ .......................................... A61K 7/13
[52] U.S. Cl. ......................... 106/498; 106/456; 106/460; 106/414; 106/453; 106/425; 106/429; 106/437; 106/438; 106/439; 106/494; 106/448; 106/450; 8/405; 8/406; 8/414; 8/416; 8/423; 424/70; 132/38
[58] Field of Search ............... 106/456, 460, 414, 453, 106/425, 429, 437, 438, 439, 447, 448, 450, 494, 498; 8/405, 406, 414, 416, 423; 424/70; 132/38

[56] References Cited

U.S. PATENT DOCUMENTS 5,205,837  4/1993  Andrean et al. .................. 8/405

FOREIGN PATENT DOCUMENTS 0220617  5/1987  European Pat. Off. .
0379409  7/1990  European Pat. Off. .
0467767  1/1992  European Pat. Off. .
2207153  1/1989  United Kingdom .

*Primary Examiner*—Mark L. Bell
*Assistant Examiner*—Scott L. Hertzog
*Attorney, Agent, or Firm*—Jacobson, Price, Holman & Stern

[57] ABSTRACT

A product in the form of colored inorganic particles including one or a number of melanin pigments, a process for its preparation and to its use, especially in the field of cosmetics, for make-up for the exoskeleton and/or for the skin, and in protecting human skin against UV radiation.

28 Claims, No Drawings

PRODUCT BASED ON COLORED INORGANIC PARTICLES INCLUDING A MELANIN PIGMENT, PROCESS FOR ITS PREPARATION AND ITS USE IN COSMETICS

The present invention relates to a product in the form of colored inorganic particles including one or a number of melanin pigments, to a process for its preparation and to its use, especially in the field of cosmetics, for make-up for the exoskeleton and/or for the skin, and in protecting human skin against UV radiation.

The color of the skin and exoskeleton, that is to say of the head hair, of the body hair and of the nails of human origin mainly arises from melanin pigments created by melanocytes.

These pigments, of natural origin, in particularly comprise black or brown pigments which are called eumelanins.

Their natural biosynthesis is carried out in a number of stages by polymerization of the oxidation products of an amino acid: tyrosine and one of these oxidation products is 5,6-dihydroxyindole which polymerizes in its turn to eumelanin.

The Applicant has described, in earlier patent applications and patents various processes which make it possible to dye human hair or the skin with 5,6-dihydroxyindole or its derivatives, using various oxidation systems. The colorings thus formed are fixed or enter into the keratinous substrate.

The hope is to be able, on certain occasions, to confer on hair a dyeing which can optionally be rapidly removed.

Pigments based on metal compounds such as, for example, black and brown iron oxides, are moreover used in make-up compositions for the skin and exoskeleton such as body hair, eyelashes or eyebrows, or nails.

The pigments which can be used for this purpose are few in number and offer a very limited pallette of colorings and, for this reason, the search is for pigments having a greater variety of colors to satisfy make-up needs and which are cosmetically acceptable.

The Applicant has discovered that it was possible to prepare a product in vitro in the form of a powder formed of colored inorganic particles and including one or a number of melanin pigments.

It was discovered that the use of the particles defined above was particularly advantageous insofar as once introduced into a cosmetically acceptable medium, they distributed themselves well in the composition which spread easily on the exoskeleton or the skin and has a significant covering ability.

It was also discovered that the combination of melanin pigments with colored inorganic particles led to pigments having a great variety of colorings particularly stable to light.

It also observed that these colored particles including melanin pigments had a particularly advantageous coefficient of absorption of ultraviolet radiation with respect to the products known thus far.

Non-white particles consisting of metal salts, insoluble in the cosmetic medium, which can be used in cosmetics, referenced in the Color Index under the "Inorganic Coloring Matters" chapter and carrying the numbers 77000 to 77947, except for the white pigments and particles existing in the lamellar form, such as lamellar iron oxide, are called "colored inorganic particles". These colored inorganic particles can consist of a single pigment or of a mixture of pigments and can thus exist in the form of pearly or interferential pigments.

The pigment formed by oxidation of 5,6-dihydroxyindole, optionally in combination with 5,6-dihydroxyindole-2-carboxylic acid, is called "melanin pigment".

By analogy and simplification, the pigment formed by oxidation of the various compounds of formula (I) defined below will be called "melanin pigment".

The subject of the present invention is thus a powder consisting of colored inorganic particles including one or a number of melanin pigments.

Another subject of the invention consists of the preparation of such a powder.

Another subject of the invention is the cosmetic application of such powders, especially in make-up products for the skin and exoskeleton and in protecting human skin against UV radiation.

Other subjects of the invention will become apparent on reading the description and examples which follow.

The product in accordance with the invention is essentially characterized in that it exists in the form of a powder consisting of colored inorganic particles whose greatest size is less than 200 microns and including in or on the particles a synthetic melanin pigment formed in situ.

The melanin pigment results from the oxidation of at least one indole compound corresponding to the formula:

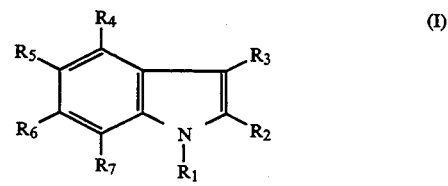

in which:

$R_1$ and $R_3$ denote, independently of each other, a hydrogen atom or a $C_1$-$C_4$ alkyl group;

$R_2$ represents a hydrogen atom, a $C_1$-$C_4$ alkyl group, a carboxyl group or a ($C_1$-$C_4$)alkoxycarbonyl group;

$R_4$ and $R_7$ denote, independently of each other, a hydrogen atom, a hydroxyl group, or a $C_1$-$C_4$ alkyl, amino, ($C_1$-$C_4$)alkoxy, ($C_2$-$C_4$)acyloxy or ($C_2$-$C_4$)acylamino group;

$R_5$ denotes hydrogen or a hydroxyl, ($C_1$-$C_4$)alkoxy, ($C_1$-$C_4$)alkyl, halo, amino, ($C_2$-$C_{14}$)acyloxy, ($C_2$-$C_4$)acylamino or trimethylsilyloxy group;

$R_6$ denotes hydrogen or a hydroxyl, ($C_1$-$C_4$)alkoxy, amino, ($C_2$-$C_4$)acyloxy, ($C_2$-$C_4$)acylamino, trimethylsilyloxy or hydroxy($C_2$-$C_4$)alkylamino group;

$R_5$ and $R_6$ can form, jointly with the carbon atoms to which they are attached, a methylenedioxy ring optionally substituted by a $C_1$-$C_4$ alkyl or $C_1$-$C_4$ alkoxy group or a carbonyldioxy ring; at least one of the groups $R_4$ to $R_7$ represents an OZ or NHR group, a single one at most of the groups $R_4$ to $R_7$ denoting NHR;

and at most two of the groups $R_4$ to $R_7$ denote OZ, in the case where Z denotes hydrogen, these groups are in position 5 and 6;

and at least one of the groups $R_4$ to $R_7$ represents hydrogen, in the case where a single one of these groups denotes hydrogen, a single group from $R_4$ to $R_7$ then denotes NHR or OZ, and the other groups denote $C_1$-$C_4$ alkyl;

R denoting, in NHR, a hydrogen atom or a $C_2$-$C_4$ acyl or $C_2$-$C_4$ hydroxyalkyl group and Z denoting, in OZ, a hydrogen atom or a $C_2$-$C_4$ acyl, $C_1$-$C_4$ alkyl or trimethylsilyl group; and the corresponding salts.

The indole compounds of formula (I) are chosen, in particular, from 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-methoxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-ethoxycarbonylindole, 7-hydroxy-3-methylindole, 5-hydroxy-6-methoxy-2,3-dimethylindole, 5-hydroxy-3-methylindole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5-methoxyindole, 6-N-$\beta$-hydroxyethylaminoindole [sic], 4-aminoindole, 5-aminoindole, 6-aminoindole, 7-aminoindole, N-methyl-6-$\beta$-hydroxyethylaminoindole [sic], 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole and 5,6-dimethoxyindole.

5,6-Dihydroxyindole, 6-hydroxyindole, 3-methyl-5,6-dihydroxyindole, 2-methyl-5,6-dihydroxyindole, 1-methyl-5,6-dihydroxyindole and 2-carboxy-5,6-dihydroxyindole, used alone or as mixtures, are particularly preferred.

The colored inorganic particles are non-white particles, preferably chosen from iron oxides, with the exception of lamellar iron oxide, ultramarine blue (which is a complex sulfosilicate), chromium oxides, manganese violet (which is an ammonium and manganese pyrophosphate) and prussian blue (which is an iron ferricyanide).

The particle size of the particles constituting the powder in accordance with the invention is a function of the particle size of the starting colored inorganic particles and can vary within wide limits ranging from 0.01 to 150 microns.

When the colored inorganic particle is a pearly or interferential pigment, the particle size of the powder including the melanin pigment varies between 10 and 150 microns.

On the other hand, when the colored inorganic particle is a metal salt, such as an iron or chromium oxide or an iron or manganese salt, the particle size of the particles including the melanin pigment constituting the powder is generally between 0.01 and 5 microns.

The product in accordance with the invention is preferably prepared according to a process consisting in mixing the indole compound of formula (I) and the colored inorganic particles defined above, in the air and at preferably ambient temperature, which can range up to 100° C., in an essentially non-solvent medium of the colored inorganic particles.

Oxidation of the indole compound of formula (I) can be carried out in aqueous or water/solvent medium in the air in the optional presence of an alkaline agent and/or of a metallic oxidation catalyst.

A preferred metallic oxidation catalyst consists of the cupric ion.

Oxidation can also be carried out by using hydrogen peroxide in the presence of an alkaline agent, such as preferably aqueous ammonia, or in the presence of an iodide ion, the iodide preferably being the iodide of an alkali or alkaline-earth metal or of ammonium.

It is also possible to carry out the oxidation using periodic acid and its water-soluble salts and derivatives, organic peracids and their persalts, permanganates and dichromates, such as those of sodium or potassium, sodium hyrdochlorite, alkaline chlorites, potassium ferricyanide, ammonium persulfate, silver oxide, lead oxide, ferric chloride, sodium nitrite, rare-earth salts, including especially cerium, and organic oxidizing agents chosen from ortho- and parabenzoquinones, ortho- and parabenzoquinone monoimines or diimines, 1,2- and 1,4-naphthoquinones, and 1,2- and 1,4-naphthoquinone mono- or diimines. The preferred salt of periodic acid is sodium periodate.

It is possible to activate the oxidizing agents with a pH-modifying agent.

For example, during use of the iodide/hydrogen peroxide system, an alkaline medium is preferably used which makes it possible to activate the reaction.

The particularly preferred process consists in using, as oxidizing agent, hydrogen peroxide at alkaline pH and in this case it is an ammoniacal medium.

The reaction medium used for forming the coloring on and in the colored particles is an essentially non-solvent medium of the colored particles under consideration. It preferably consists of water and can optionally consist of a mixture of water and solvent(s). The solvent is chosen so that it rapidly solubilizes the indole compound of formula (I).

Among these solvents, there may be mentioned, by way of example, lower $C_1$-$C_4$ alcohols such as ethyl alcohol, propyl or isopropyl alcohol, or tert-butyl alcohol, alkylene glycols such as ethylene glycol or propylene glycol, alkyl ethers of alkylene glycols such as the monomethyl, monoethyl and monobutyl ethers of ethylene glycol or the monomethyl ethers of propylene glycol and of dipropylene glycol, and methyl lactate.

When the medium consists of a water/solvent(s) mixture, the solvent(s) is (are) present in concentrations between 0.5 and 90% by weight with respect to the total weight of the composition, in particular between 2 and 50% by weight and preferably between 2 and 20% by weight.

Their nature is chosen and their proportion is adjusted according to the solubility criteria of the indole derivatives of formula (I) and to the insolubility criterion of the colored particles including the melanin pigment.

In the process for the preparation of the products in the form of particles in accordance with the invention, the indole compound is preferably used in proportions by weight between 0.1 and 10% and preferably between 0.5 and 7% by weight with respect to the total weight of the reaction mixture, the colored filler representing 0.05 to 70% by weight of the reaction mixture, the remainder of the reaction mixture generally consisting of water or a water/solvent(s) mixture.

The oxidizing agents are used in amounts sufficient to form, by oxidation, the melanin pigment.

When the iodide ion is used to form the melanin pigment, this is preferably used in proportions between 0.07 and 4% and in particular between 0.7 and 3%, an indole compound/I$^-$ ratio between 0.6 and 6 and more particularly between 3 and 4 being observed.

The proportions are determined with respect to the weight of the reaction mixture.

The powder consisting of colored inorganic particles including the melanin pigment is isolated from the reaction mixture by filtration or by centrifuging, washed with water and then, optionally, dried and/or lyophilized.

The powder in the form of colored inorganic particles and including the melanin pigment as defined above can be added to conventional cosmetic substrates at a concentration between 0.05 and 35% by weight and preferably between 0.1 and 20% by weight with respect to the total weight of the composition to lead to cosmetic compositions which protect the human skin, make-up products such as for the eyelashes, the eyebrows, the skin, hair or nails, such as eyeshadows, rouges, liners, also called "eye-liners", mascaras for the eyelashes and eyebrows, nail varnishes or also temporary hair dyeing compositions. These cosmetic substrates are known in themselves.

The medium used in these various cosmetic compositions is an essentially non-solvent medium of the colored inorganic particles including the melanin pigment. A medium is called essentially non-solvent which dissolves less than 1% by weight of the colored inorganic particles.

The compositions can be provided in particular in the lotion, thickened lotion, gel, cream, milk, powder or stick form and can optionally be packaged in aerosols and be provided in the foam or spray form.

When the compositions are used for making up the skin, hair, eyelashes and eyebrows, they can especially be provided in the anhydrous or aqueous, solid or pasty form as oil-in-water or water-in-oil emulsions or also as suspensions. These compositions have the advantage of being stable and of being highly innocuous.

When the compositions are used for protecting human skin against UV radiation, they constitute compositions known as "anti-sun" and they can be provided in the form of suspensions or dispersions in solvents or fats, or also in the form of emulsions such as creams and milks, ointments, gels, solid sticks and aerosol foams.

In all cases, when they are used in the form of emulsions, they can additionally contain surface-active agents which are well known in the state of the art, such as anionic, nonionic, cationic or amphoteric surface-active agents.

The make-up compositions and the anti-sun compositions can also contain fats, organic solvents, silicones, thickening agents, softening agents, sunscreening agents, antifoaming agents, hydrating agents, fragrances, preserving agents, antioxidizing agents, fillers, sequestering agents, treatment agents such as anionic, cationic, nonionic or amphoteric polymers or their mixtures, propellants, or basifying or acidifying agents.

The fats can consist of an oil or a wax or a mixture thereof, fatty acids, fatty alcohols, petroleum jelly, paraffin, lanolin, hydrogenated lanolin or acetylated lanolin.

The oils are chosen from animal, vegetable, inorganic or synthetic oils and especially hydrogenated palm oil, hydrogenated castor oil, liquid paraffin, paraffin oil or purcellin oil.

The waxes are chosen from animal, fossil, vegetable, mineral or synthetic waxes. Beeswaxes, carnauba, candellila [sic], sugar cane and Japan waxes, ozokerites, montan wax, microcrystalline waxes and paraffin waxes may be especially mentioned.

When compositions are used for coloring the nails, they are provided in the form of products known as "nail varnishes", containing the powder in accordance with the invention in the dispersed form in a cosmetically acceptable solvent containing one or a number of resins and ingredients commonly used in this type of product.

The compositions in accordance with the invention can also contain, in addition to the colored inorganic particles including melanin pigments, as defined above, other pigments generally used in cosmetics, especially white pigments or pearly and/or pearlescence pigments, which make it possible to vary the colorings capable of being obtained or to increase protection with respect to ultraviolet radiation. In the latter case, nanopigments of metal oxides such as titanium, zinc, cerium or zirconium oxides, with a mean diameter of less than 100 nm and preferably between 5 and 50 nm, are used. The nanopigments can be coated or noncoated.

The coated pigments are pigments which have been subjected to one or a number of surface treatments of chemical, electronic, mechanochemical and/or mechanical nature with compounds as described, for example, in Cosmetics and Toiletries, February 1990, Vol. 105, pages 53–64, such as amino acids, beeswax, fatty acids, fatty alcohols, anionic surface-active agents, lecithins, sodium, potassium, zinc, iron or aluminum salts of fatty acids, metal alkoxides (of titanium or aluminum), polyethylene, silicones, proteins (collagen, elastin), alkanolamines, silicone oxides, metal oxides or sodium hexametaphosphate.

Another subject of the invention is a process for temporary hair dyeing, for making up the skin, eyelashes and eyebrows or nails, or for protecting the human skin against the harmful effects of UV radiation, using a powder based on colored inorganic particles including melanin pigments as defined above, this powder being applied directly or by means of cosmetic compositions as defined above.

The following examples are intended to illustrate the invention without having any limiting nature.

PREPARATION EXAMPLES

Example 1

20 g (0.134 mol) of 5,6-dihydroxyindole are solubilized in 400 ml of a 0.1% aqueous ammonia solution. 180 g of ultramarine blue (CI 77007) are added to this mixture. The suspension is stirred for 15 minutes and is then brought to 80° C. 134.57 g of hydrogen peroxide containing 10.2 g (0.3 mol) of hydrogen peroxide solution are added over 60 minutes while maintaining the temperature between 80° and 85° C. On completion of the addition, the temperature is maintained at 80° C. for 2 hours and the reaction mixture is then cooled to 10° C. The product is filtered off and washed with water. After drying, 199 g of dark-blue powder are obtained.

Example 2

20 g (0.134 mol) of 5,6-dihydroxyindole are solubilized in 100 ml of a 0.1% aqueous ammonia solution. 180 g of hydrated chromium oxide (CI 77289) are added to this mixture. The suspension is stirred for 15 minutes and is then brought to 80° C. 134.57 g of hydrogen peroxide solution containing 10.2 g (0.3 mol) of hydrogen peroxide are added over 60 minutes while maintaining the temperature between 80° and 85° C. On completion of the addition, the temperature is maintained at 80° C. for 2 hours and the reaction mixture is then cooled to 10° C. The product is filtered off and washed with water. After drying, 198 g of dark-green powder are obtained.

Example 3

23.34 g (0.156 mol) of 5,6-dihydroxyindole are solubilized in 486 ml of a 0.1% aqueous ammonia solution. 210 g of red iron oxide, which is a mixture of yellow iron oxide (CI 77492) and brown iron oxide (CI 77491), are added to this mixture and the suspension is stirred for 15 minutes and is then brought to 80° C. 168 g of hydrogen peroxide solution containing 12.59 g (0.37 mol) of hydrogen peroxide are added over 1 hour while maintaining the temperature between 80° and 85° C. On completion of the addition, the temperature is maintained at 80° C. for 1 hour and the reaction mixture is then cooled to 20° C. The precipitate is filtered off and washed with water. After drying, 229 g of dark-brown powder are obtained.

Example 4

20 g (0.134 mol) of 5,6-dihydroxyindole are solubilized in 400 ml of a 0.1% aqueous ammonia solution. 180 g of chromium oxide (CI 77288) are added to this mixture. The suspension is stirred for 15 minutes and is then brought to 80° C. 134.6 g of hydrogen peroxide solution containing 10.2 g (0.3 mol) of hydrogen peroxide are added over 1 hour while maintaining the temperature between 80° and 85° C. On completion of the addition, the temperature is maintained at 80° C. for 2 hours and the reaction mixture is then cooled to 20° C. The product is centrifuged and washed with water. After lyophilization, 195 g of dark-green powder are obtained.

Example 5

20 g (0.123 mol) of 5,6-dihydroxyindole-3-methylindole are solubilized in 400 ml of a 0.1% aqueous ammonia solution. 180 g of black iron oxide (CI 77499) are added to this mixture. The suspension is stirred for 15 minutes and is then brought to 80° C. 134 g of hydrogen peroxide solution containing 9.34 g of hydrogen peroxide are added over 1 hour while maintaining the temperature between 80° and 85° C. On completion of the addition, the temperature is maintained at 80° C. for 2 hours and the reaction mixture is then cooled to 20° C. The product is centrifuged and washed with water. After lyophilization, 196 g of dark-brown powder are obtained.

Example 6

3 g ($2 \cdot 10^{-2}$ mol) of 5,6-dihydroxyindole are solubilized in 200 ml of a 0.1% aqueous ammonia solution. 97 g of prussian blue (CI 77510) are added to this mixture. The suspension is stirred for 15 minutes and is then brought to 80° C. 20.2 g of hydrogen peroxide solution containing 1.55 g ($4.57 \cdot 10^{-2}$ mol) of hydrogen peroxide are added over 30 minutes while maintaining the temperature between 80° and 85° C. On completion of the addition, the temperature is maintained at 80° C. for 1 hour and the reaction mixture is then cooled to 20° C. The product is centrifuged and washed with water. After lyophilization, 88.5 g of blue powder are obtained.

Example 7

10 g (0.067 mol) of 5,6-dihydroxyindole are solubilized in 400 ml of a 0.1% aqueous ammonia solution. 190 g of titanium-mica, sold by the Company Merck under the name Colorona dark blue (mixture of pigments: CI 77019, CI 77891 and CI 77510), are added to this mixture. The suspension is stirred for 15 minutes and is then brought to 80° C. 67.3 g of hydrogen peroxide solution containing 5.19 g (0.15 mol) of hydrogen peroxide are added over 30 minutes while maintaining the temperature between 80° and 85° C. On completion of the addition, the temperature is maintained at 80° C. for 2 hours and the reaction mixture is then cooled. The product is centrifuged and washed with water. After lyophilization, 199 g of dark-blue powder are obtained.

Example 8

4.4 g (0.03 mol) of 5,6-dihydroxyindole are solubilized in 88 ml of a 0.1% aqueous ammonia solution. 40 g of black iron oxide are added to this mixture. The suspension is stirred for 15 minutes and is then brought to 80° C. 26.8 g of hydrogen peroxide solution containing 6.7 g (0.2 mol) of hydrogen peroxide are added over 60 minutes while maintaining the temperature between 80° C. and 85° C. On completion of the addition, the temperature is maintained at 80° C. for approximately 2 hours and the reaction mixture is then cooled with ice. The suspension obtained is centrifuged and then washed with water. After lyophilization, 41.07 g of black powder are obtained.

Example 9

5 g (0.034 mol) of 5,6-dihydroxyindole are solubilized in 200 ml of a 0.1% aqueous ammonia solution. 95 g of ultramarine blue are added to this mixture. The suspension is stirred for 15 minutes and is then brought to 80° C. 30.4 g of hydrogen peroxide solution containing 2.3 g (0.067 mol) of hydrogen peroxide are added while maintaining the temperature between 80° and 85° C. On completion of the addition, the temperature is maintained at 80° C., stirring is maintained for 2 hours and the reaction mixture is then cooled to 20° C. The product is centrifuged and washed with water. After lyophilization, 91.11 g of blue powder are obtained.

Example 10

2.5 g (0.017 mol) of 5,6-dihydroxyindole are solubilized in 200 ml of a 0.1% aqueous ammonia solution. 97.5 g of ultramarine blue are added to this mixture. The suspension is stirred for 15 minutes and is then brought to 80° C. 15.2 g of hydrogen peroxide solution containing 1.22 g (0.036 mol) of hydrogen peroxide are added portionwise while maintaining the temperature between 80° and 85° C. On completion of the addition, stirring is maintained and the temperature is maintained at 80° C. for 2½ hours. The reaction mixture is cooled to 20° C. The product is centrifuged and washed with water. After lyophilization, 91.85 g of blue powder are obtained.

Example 11

1 g ($6.7 \cdot 10^{-3}$ mol) of 5,6-dihydroxyindole is solubilized in 200 ml of a 0.1% aqueous ammonia solution. 99 g of ultramarine blue are added to this mixture. The suspension is stirred for 15 minutes and is then brought to 80° C. 6.1 g of hydrogen peroxide solution containing 0.44 g (0.013 mol) of hydrogen peroxide are added portionwise while maintaining the temperature between 80° and 85° C. On completion of the addition, stirring is maintained and the temperature is maintained at 80° C. for 2½ hours. The reaction mixture is cooled to 20° C. The product is centrifuged and washed with water. After lyophilization, 96.18 g of blue powder are obtained.

Example 12

5 g (0.034 mol) of 5,6-dihydroxyindole are solubilized in 200 ml of a 0.1% aqueous ammonia solution. 95 g of hydrated chromium oxide are added to this mixture. The suspension is stirred for 15 minutes and is then brought to 80° C. The reaction is then carried out as in Example 9. After lyophilization, 96.87 g of dark-green powder are obtained.

Example 13

5 g (0.034 mol) of 5,6-dihydroxyindole are solubilized in 200 ml of a 0.1% aqueous ammonia solution. 95 g of red iron oxide, which is a mixture of yellow iron oxide (CI 77492) and brown iron oxide (CI 77491), are added to this mixture and the suspension is stirred for 15 minutes and then brought to 80° C. The reaction is then carried out as in Example 9. After lyophilization, 98.09 g of brown powder are obtained.

Example 14

2.5 g (0.017 mol) of 5,6-dihydroxyindole are solubilized in 200 ml of a 0.1% aqueous ammonia solution. 97.5 g of red iron oxide, as described in the preceding example, are added to this mixture and the suspension is stirred for 15 minutes and then brought to 80° C. The reaction is then carried out as in Example 10. After lyophilization, 83.2 g of brown powder are obtained.

Example 15

20 g (0.134 mol) of 5,6-dihydroxyindole are solubilized in 400 ml of a 0.1% aqueous ammonia solution. 180 g of manganese violet (CI 77742) are added to this mixture. The reaction is then carried out as shown in Example 1. After drying, 189.64 g of purple-gray powder are obtained.

COMPOSITION EXAMPLES

Composition Example 1

Composition for Making Up Hair

The following composition is prepared:

| | | |
|---|---|---|
| Crosslinked methacrylic acid/ ethyl acrylate copolymer as an aqueous dispersion containing 38% AM, sold under the name Viscoatex 538 by the Company Coatex | | 3.95 g |
| Hydroxyethylcellulose/diallyldimethylammonium chloride copolymer, sold under the name Celquat LOR by the company National Starch | | 1.5 g |
| Colored powder of Example 2 | | 1.0 g |
| Preserving agent | | 0.15 g |
| 2-amino-2-methyl-1-propanol | q.s. pH = | 7.5 |
| Demineralized water | q.s. for | 100 g |

This gelled composition, applied to hair, confers an almond-green tint on it.

Composition Example 2

Composition for Making Up Hair

The following composition is prepared:

| | | |
|---|---|---|
| Viscoatex 538 sold by the Company Coatex | | 3.95 g |
| Celquat LOR sold by the Company National Starch | | 1.5 g |
| Cationic emulsion containing 35% polydimethylsiloxane containing aminoethylpropylamine groups, sold under the name DC 929 by the company Dow Corning | | 0.85 g |
| Colored powder of Example 1 | | 1.0 g |
| Preserving agent | | 0.25 g |
| Sequestering agent | | 0.2 g |
| Ethanol | | 10.0 g |
| 2-Amino-2-methyl-1-propanol | q.s. pH = | 7.5 |
| Demineralized water | q.s. for | 100 g |

This gelled composition is applied to hair and confers a bluish-gray tint on it.

Composition Example 3

Composition for Making Up Hair

The following composition is prepared:

| | | |
|---|---|---|
| Viscoatex 538 sold by the Company Coatex | | 3.85 g |
| Celquat LOR sold by the Company National Starch | | 1.5 g |
| Colored powder of Example 3 | | 1.0 g |
| Ethanol | | 10.0 g |
| Preserving agent | | 0.25 g |
| Fragrance | | 0.3 g |
| 2-Amino-2-methyl-1-propanol | q.s. pH = | 7.5 |
| Demineralized water | q.s. for | 100 g |

This gelled composition confers a red-chestnut color on hair.

Composition Example 4

A nail varnish is prepared of the following composition:

| | | |
|---|---|---|
| Nitrocellulose | | 10.90 g |
| Toluenesulfonamide formaldehyde [sic] resin | | 9.85 g |
| Tributyl acetylcitrate | | 6.50 g |
| Butyl acetate | | 21.80 g |
| Ethyl acetate | | 9.40 g |
| Isopropyl alcohol | | 7.80 g |
| Stearalkonium hectorite | | 1.36 g |
| Pigments: | | |
| Ultra-marine blue | | 0.01 g |
| Titanium dioxide | | 0.27 g |
| DC Red 34 | | 0.07 g |
| Colored powder of Example 3 | | 0.30 g |
| Pearlescance agents (titanium-mica) | | 0.60 g |
| Citric acid | | 0.06 g |
| Toluene | q.s. for | 100 g |

This varnish confers a pearly-brown color on the nails.

Composition Example 5

A make-up foundation of the following composition is prepared:

| | | |
|---|---|---|
| Glyceryl stearate | | 2.2 g |
| Mixture of capric and caprylic acid and of glycerol triester | | 15.0 g |
| Colored powder of Example 3 | | 9.0 g |
| Methyl parahydroxybenzoate | | 0.1 g |
| Propyl parahydroxybenzoate | | 0.1 g |
| Preserving agent | | 0.3 g |
| 2-Hydroxy-4-methoxybenzophonone | | 0.5 g |
| Octyl dimethyl p-aminobenzoate | | 0.5 g |
| Aluminum magnesium silicate | | 1.0 g |
| Triethanolamine | | 1.0 g |
| Carboxymethylcellulose | | 0.16 g |
| Aluminum salt of the product of reaction of octenylsuccinic anhydride and starch, sold under the name Dry Flo by the Company National Starch | | 5.0 g |
| Cyclic polydimethylsiloxane sold under the name Silbione Oil 70045 by the Company Rhône-Poulenc | | 10.0 g |
| Propylene glycol | | 2.0 g |
| Glycerol | | 3.0 g |
| Sodium lauroyl sarcosinate | | 0.6 g |
| Stearic acid | | 2.2 g |
| Water | q.s. for | 100 g |

The make-up foundation obtained is natural beige.

Composition Example 6

A compacted body powder of the following composition is prepared:

| | | |
|---|---|---|
| Zinc stearate | | 6.0 g |
| Propyl parahydroxybenzoate | | 0.2 g |
| Fragrance | | 4.0 g |
| Colored powder of Example 3 | | 0.07 g |
| Talc | q.s. for | 100 g |

This natural beige powder is applied to the body with a powder puff.

Composition Example 7

An eyeshadow, in the form of a compacted powder, of the following composition is prepared:

| | | |
|---|---|---|
| Polyamide powder | | 15.0 g |
| Cyclic polydimethylsiloxane sold under the name Silbione Oil by the Company Rhône-Poulenc | | 9.0 g |
| Pearlescence agent: Titanium-mica | | 30.0 g |
| Colored powder of Example 2 | | 7.0 g |
| Colored powder of Example 1 | | 6.0 g |
| Talc | q.s. for | 100 g |

This eyeshadow has a green-blue color and is applied using a brush or a foam applicator.

Composition Example 8

A waterproof mascara of the following composition is prepared:

| | | |
|---|---|---|
| Carnauba wax | | 5.0 g |
| Candelilla wax | | 5.0 g |
| Ethyl alcohol | | 3.0 g |
| Montmorillonite modified with an organic substance | | 4.0 g |
| Lanolin | | 2.0 g |
| Talc | | 10.0 g |
| Colored powder of Example 3 | | 10.0 g |
| Isoparaffin | q.s for | 100 g |

The procedure is the following:

The waxes are heated to 80° C. The talc and the pigments are added. The Montmorillonite, which has been modified with an organic substance, and part of the isoparaffin are then incorporated. The ethyl alcohol and the remainder of the isoparaffin are introduced at approximately 40° C. The whole mixture is transferred to a grinder.

This waterproof masquara [sic] is easy to apply and colors the eyelashes brown.

Composition Example 9

A mascara of the following composition is prepared:

| | | |
|---|---|---|
| Triethanolamine stearate | | 15.0 g |
| Beeswax | | 8.0 g |
| Paraffin | | 3.0 g |
| Rosin | | 2.0 g |
| Ozokerite | | 10.0 g |
| Propyl parahydroxybenzoate | | 0.20 g |
| Methyl parahydroxybenzoate | | 0.20 g |
| Gum arabic | | 0.50 g |
| Keratin hydrolysate | | 1.0 g |
| Black iron oxide | | 5.0 g |
| Colored powder of Example 2 | | 5.0 g |
| Water | q.s. for | 100 g |

This mascara, in the emulsion form, is prepared in the following way:

The waxes are melted. The pigments are incorporated. The aqueous phase, containing the gum arabic and the keratin hydrolysate, is heated to the same temperature as the waxy phase. The two phases are mixed and stirred vigorously.

The mascara obtained confers, on the eyelashes, a gray-blue color with faint metallic highlights.

Composition Example 10

A rouge, in the compacted powder form, of the following composition is prepared:

| | | |
|---|---|---|
| Titanium dioxide | | 10.0 g |
| Titanium-mica | | 10.0 g |
| DC Red 30 | | 1.2 g |
| Propyl parahydroxybenzoate | | 0.2 g |
| Liquid paraffin | | 6.0 g |
| 2-Hydroxy-4-methoxybenzophenone sold under the name Uvinul M-40 by the Company BASF | | 0.5 g |
| Colored powder of Example 3 | | 3.0 g |
| Talc | q.s. for | 100 g |

This rouge of orangey-brown color is applied with a brush.

Composition Example 11

A pressed powder for the face of the following composition is prepared:

| | | |
|---|---|---|
| Polyethylene powder | | 5.0 g |
| Colored powder of Example 3 | | 6.0 g |
| Titanium dioxide | | 10.0 g |
| Mica | | 15.0 g |
| Isopropyl myristate | | 1.5 g |
| Liquid paraffin | | 1.5 g |
| Sorbitol | | 0.5 g |
| Talc | q.s. for | 100 g |

This powder, of natural beige color, is applied to the face using a powder puff or a brush,

Composition Example 12

An anti-sun composition containing the constituents below is prepared:

| | | |
|---|---|---|
| Mixture of cetearyl alcohol and of cetearyl alcohol oxyethylenated with 33 mols of ethylene oxide (80/20) | | 7.0 g |
| Glyceryl stearate sold under the name Geleol by the Company Gattefosse | | 2.0 g |
| Pure cetyl alcohol | | 1.5 g |
| Polydimethylsiloxane sold under the name Silbione Oil 70047 V 300 by the Company Rhône-Poulenc | | 1.5 g |
| Liquid paraffin | | 15.0 g |
| Butyl p-hydroxybenzoate | | 0.2 g |
| Colored powder of Example 3 | | 0.15 g |
| Glycerol | | 20.0 g |
| Imidazolidinylurea | | 0.2 g |
| Sterilized demineralized water | q.s. for | 100 g |

Composition Example 13

A make-up composition for the eyelashes is prepared which contains the constituents below:

| | | |
|---|---|---|
| Crosslinked acrylates/$C_8$–$C_{30}$ alkyl acrylate copolymer | | 0.1 g |
| Crosslinked carboxyvinyl copolymer, sold under the name Carbopol 940 by the Company Goodrich Chemical | | 0.6 g |
| Triethanolamine | | 0.8 g |
| Glycerol | | 2.0 g |
| Preserving agent | | 0.2 g |
| Octamethylcyclosiloxane | | 25.0 g |
| Black iron oxide | | 5.0 g |
| Colored powder of Example 9 | | 5.0 g |
| Water | q.s. for | 100 g |

The polymers are dispersed while hot with the preserving agents in water to form a gel. The glycerol and the triethanolamine are added. The pigment is dispersed in the silicone and added to the gelled phase.

A navy-blue gelled emulsion for making up eyelashes is obtained.

Composition Example 14

A lipstick of the following composition is prepared:

| | | |
|---|---|---|
| 2,6-Di-tert-butyl-p-cresol | | 0.16 g |
| Liquid lanolin | | 17.5 g |
| Microcrystalline wax | | 15.0 g |
| Triglycerides of carprylic [sic] and capric acids | | 11.0 g |
| Glyceryl octyl behenate | | 11.0 g |
| Colored powder of Example 14 | | 3.0 g |
| Titanium-mica | | 6.0 g |
| Castor oil | q.s. for | 100 g |

A lipstick of a pearly-brown color is obtained.

Composition Example 15

A rouge, in the compacted powder form, of the following composition is prepared:

| | | |
|---|---|---|
| Titanium dioxide | | 10.0 g |
| Titanium mica | | 10.0 g |
| DC Red 30 | | 1.2 g |
| Propyl parahydroxybenzoate | | 0.2 g |
| Liquid paraffin | | 6.0 g |
| 2-Hydroxy-4-methoxybenzophenone, sold under the name Uvinul M-40 by the Company BASF | | 0.5 g |
| Colored powder of Example 13 | | 1.0 g |
| Talc | q.s. for | 100 g |

This rouge of orangey-brown color is applied with a brush.

Composition Example 16

A make-up foundation of the following composition is prepared:

| | | |
|---|---|---|
| Glyceryl stearate | | 2.2 g |
| Mixture of capric and caprylic acids and of glycerol triester | | 15.0 g |
| Titanium oxide | | 10.53 g |
| Yellow iron oxide | | 0.83 g |
| Colored powder of Example 5 | | 0.14 g |
| Colored powder of Example 14 | | 0.50 g |
| Methyl parahydroxybenzoate | | 0.1 g |
| Propyl parahydroxybenzoate | | 0.1 g |
| Preserving agent | | 0.3 g |
| 2-Hydroxy-4-methoxybenzophonone | | 0.5 g |
| Octyl dimethyl p-aminobenzoate | | 0.5 g |
| Aluminum magnesium silicate | | 1.0 g |
| Triethanolamine | | 1.0 g |
| Carboxymethylcellulose | | 0.16 g |
| Aluminum salt of the product of reaction of octenylsuccinic anhydride and starch, sold under the name Dry Flo by the Company National Starch | | 5.0 g |
| Cyclic polydimethylsiloxane, sold under the name Silbione Oil 70045 by the Company Rhône-Poulenc | | 10.0 g |
| Propylene glycol | | 2.0 g |
| Glycerol | | 3.0 g |
| Sodium lauroyl sarcosinate | | 0.6 g |
| Stearic acid | | 2.2 g |
| Water | q.s. for | 100 g |

The make-up foundation obtained is natural beige.

Composition Example 17

An eyeshadow, in the compacted powder form, of the following composition is prepared:

| | | |
|---|---|---|
| Polyamide powder | | 15.0 g |
| Cyclic polydimethylsiloxane, sold under the name Silbione Oil by the Company Rhône-Poulenc | | 9.0 g |
| Pearlescence agent: Titanium-mica | | 30.0 g |
| Colored powder of Example 4 | | 7.0 g |
| Colored powder of Example 15 | | 6.0 g |
| Talc | q.s. for | 100 g |

This eyeshadow has a yellow-green color and is applied using a brush or a foam applicator.

We claim:

1. Product in the powder form consisting of particles, the particles being non-white and colored particles, with the exception of lamellar iron oxide, having a particle size of less than 200 microns and including in and/or on the particles a synthetic melanin pigment, formed in situ by oxidation of an indole compound.

2. Product according to claim 1, wherein the indole compound corresponds to the formula (I):

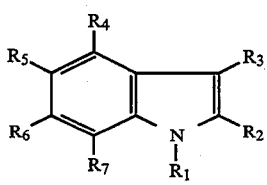 (I)

in which:
- R₁ and R₃ denote, independently of each other, a hydrogen atom or a $C_1$-$C_4$ alkyl group;
- R₂ represents a hydrogen atom, a $C_1$-$C_4$ alkyl group, a carboxyl group or a ($C_1$-$C_4$)alkoxycarbonyl group;
- R₄ and R₇ denote, independently of each other, a hydrogen atom, a hydroxyl group, or a $C_{1-4}$ alkyl, amino, ($C_1$-$C_4$)alkoxy, ($C_2$-$C_4$)acyloxy or ($C_2$-$C_4$)acylamino group;
- R₅ denotes hydrogen or a hydroxyl, ($C_1$-$C_4$)alkoxy ($C_1$-$C_4$)alkyl, halo, amino, ($C_2$-$C_4$)acyloxy, ($C_2$-$C_4$)acylamino or trimethylsilyloxy group;
- R₆ denotes hydrogen or a hydroxyl, ($C_1$-$C_4$)alkoxy, amino, ($C_2$-$C_4$)acyloxy, ($C_2$-$C_4$)acylamino, trimethylsilyloxy or hydroxy($C_2$-$C_4$)alkylamino group;
- R₅ and R₆ can form, jointly with the carbon atoms to which they are attached, a methylenedioxy ring which is unsubstittued or substituted by a $C_1$-$C_4$ alkyl or $C_1$-$C_4$ alkoxy group or a carbonyldioxy ring; at least one of the groups R₄ to R₇ represents an OZ or NHR group, a single one at most of the groups R₄ to R₇ denoting NHR;
- and at most two of the groups R₄ to R₇ denote OZ, in the case where Z denotes hydrogen, these groups are in position 5 and 6;
- and at least one of the groups R₄ to R₇ represents hydrogen, in the case where a single one of these groups denotes hydrogen, a single group from R₄ to R₇ then denotes NHR or OZ, and the other groups denote $C_1$-$C_4$ alkyl;
- R denoting, in NHR, a hydrogen atom or a $C_2$-$C_4$ acyl or $C_2$-$C_4$ hydroxyalkyl group and Z denoting, in OZ, a hydrogen atom or a $C_2$-$C_{14}$ acyl, $C_1$-$C_4$ alkyl or trimethylsilyl group;

and the corresponding salts.

3. Product according to claim 1, wherein the indole compound is 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-methoxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy 2,3-dimethylindole, 6-hydroxy-2-ethoxycarbonylindole, 7-hydroxy-3-methylindole, 5-hydroxy-6-methoxy-2,3-dimethylindole, 5-hydroxy-3-methylindole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5-methoxyindole, 6-N-β-hydroxyethylaminoindole, 4-aminoindole, 5-aminoindole, 6-aminoindole, 7-aminoindole, N-methyl-6-β-hydroxyethylaminoindole, 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole or 5,6-dimethoxyindole.

4. Product according to claim 1, wherein the indole compound is 5,6-dihydroxyindole, 6-hydroxyindole, 3-methyl-5,6-dihydroxyindole, 2-methyl-5,6-dihydroxyindole, 1-methyl-5,6-dihydroxyindole, 2-carboxy-5,6-dihydroxyindole or mixtures thereof.

5. Product according to claim 1, wherein the colored inorganic particles are iron oxides, with the exception of lamellar iron oxide, complex sulfosilicate, chromium oxides, ammonium or manganese pyrophosphates or iron ferricyanide.

6. Product according to claim 1, the colored inorganic particles have a size between 0.01 and 150 microns.

7. Process for the preparation of product as defined in claim 2, wherein the indole compound of formula (I) and colored inorganic particles, having a size of less than 200 microns, are mixed in an aqueous medium and the melanin pigment is then formed by oxidation of the indole compound of formula (I).

8. Process according to claim 7, wherein oxidation is carried out slowly in air at alkaline pH.

9. Process according to claim 7, wherein oxidation is carried out by the oxygen of the air in the presence of a metal catalyst.

10. Process according to claim 7, wherein oxidation is carried out by the addition of oxidizing agents consisting of hydrogen peroxide, organic peracids or their persalts, periodic acid or its salts, permanganates, dichromates, sodium hypochlorite, alkaline chlorites, potassium ferricyanide, ammonium persulfate, silver oxide, lead oxide, ferric chloride, sodium nitrite, rare-earth salts or organic oxidizing agents which are ortho- or parabenzoquinones, ortho- or parabenzoquinone monoimines or diimines, 1,2- or 1,4-naphthoquinones, or 1,2- or 1,4-naphthoquinone mono- or diimines.

11. Process according to claim 7, wherein oxidation is carried out by hydrogen peroxide in ammoniacal medium.

12. Process according to claim 7, wherein the reaction medium is an essentially non-solvent medium of the particles and an essentially solvent medium of the indole compound of formula (I), and in that it consists of water or a mixture of water and one or more salt(s).

13. Process according to claim 7, wherein the solvent is ethyl alcohol, propyl or isopropyl alcohol, tert-butyl alcohol, alkylene glycols, alkyl ethers of alkylene glycols or methyl lactate.

14. Process according to claim 7, wherein the indole compound is used in proportions by weight between 0.1 and 10% with respect to the total weight of the reaction mixture and the colored inorganic particles are used in proportions between 0.05 and 70% by weight.

15. Cosmetic composition, comprising in a cosmetically acceptable medium, at least one product as defined in claim 1.

16. Composition according to claim 15, wherein the composition is in the form of a lotion, thickened lotion, gel, cream, milk, powder or stick form.

17. Composition according to claim 15, wherein the composition is in a form for making up the skin, hair, nails, eyelashes or eyebrows, and is provided in an anhydrous or aqueous, liquid, solid or paste form.

18. Composition according to claim 15, intended to protect human skin against UV solar radiation, wherein the composition it is provided in the foam of a suspension or dispersion in solvents or fats, or in the form of emulsions, ointments, gels, solid sticks or aerosol foams.

19. Composition according to claim 15, characterized in that it contains fats, organic solvents, silicones, thickening agents, softening agents, surface-active agents, sunscreening agents, antifoaming agents, hydrating agents, fragrances, preserving agents, antioxidizing agents, fillers, sequestering agents, treatment agents, propellants, basifying or acidifying agents or other pigments.

20. Composition according to claim 19, further comprising nanopigments of titanium, zinc, cerium or zirconium oxides, these nanopigments having a mean diameter of less than 100 nm, and being coated or noncoated.

21. Composition according to claim 15, wherein the powder in the form of colored inorganic particles including the melanin pigment is present in concentrations between 0.05 and 35% by weight with respect to the total weight of the composition.

22. A method of using the product as defined in claim 1, comprising applying the product to human skin.

23. A method of using the product as defined in claim 1, comprising making up the skin, hair, nails, eyelashes or eyebrows with the product.

24. Process according to claim 14, wherein the indole compound is used in proportions by weight between 0.5 and 7% with respect to the total weight of the reaction mixture.

25. Composition according to claim 16, wherein the composition is packaged in an aerosol in spray or foam form.

26. Composition according to claim 21, wherein the powder is present in concentrations between 0.1 and 20% by weight with respect to the total weight of the composition.

27. Product according to claim 1, wherein the indole compound is 5,6-dihydroxyindole.

28. Product according to claim 1, wherein the particles are non-white and colored particles, with the exception of lamellar particles.

* * * * *